United States Patent [19]

Mallikarjuna et al.

[11] Patent Number: 6,031,141
[45] Date of Patent: Feb. 29, 2000

[54] FLUOROOLEFIN MANUFACTURING PROCESS

[75] Inventors: Rao V.N. Mallikarjuna, Wilmington, Del.; Munirpallam A. Subramanian, Kennett Square, Pa.

[73] Assignee: E. I. du Pont de Nemours and Company, Wilmington, Del.

[21] Appl. No.: 09/129,821

[22] Filed: Aug. 6, 1998

Related U.S. Application Data

[60] Provisional application No. 60/056,793, Aug. 25, 1997.

[51] Int. Cl.$^7$ .............................. C07C 21/18; C07C 17/25
[52] U.S. Cl. .......................... 570/136; 570/155; 570/156; 570/171
[58] Field of Search ................................ 570/136, 155, 570/156

[56] References Cited

U.S. PATENT DOCUMENTS

| | | | |
|---|---|---|---|
| 2,599,631 | 6/1952 | Harmon | 260/653 |
| 2,745,886 | 5/1956 | Ruh et al. | 260/653 |
| 3,673,113 | 6/1972 | Naito et al. | 252/441 |
| 4,034,070 | 7/1977 | Wojtowicz et al. | 423/489 |
| 4,053,530 | 10/1977 | Schindel | 260/653.8 |
| 4,465,786 | 8/1984 | Zimmer et al. | 502/169 |
| 4,741,893 | 5/1988 | Watanabe et al. | 423/471 |
| 5,461,177 | 10/1995 | Manzer et al. . | |

FOREIGN PATENT DOCUMENTS

| | | | |
|---|---|---|---|
| 2900854 | 7/1979 | Germany | 423/489 |
| WO 93/25506 | 12/1993 | WIPO | C07C 17/20 |
| WO 94/06558 | 3/1994 | WIPO | B01J 23/92 |
| WO 96/05157 | 2/1996 | WIPO | C07C 17/25 |
| WO 97/07052 | 2/1997 | WIPO | C01B 7/19 |

OTHER PUBLICATIONS

P. Daniel et al., Raman–scattering study of crystallized MF3 compounds (M=Al, Cr, GA, V, Fe, In): An approach to the short–range–order force constants, *The American Physical Society*, 42, 10545–10552, 1 Dec. 1990.

Keshav N. Shrivastava, Theory of the –electron spin density dur to the Cr3+ ion and Cr3+ ion pair in a cubic fluoride lattice, *Physical Review*, 20, 5375–5378, Dec. 15, 1979.

Kerro Knox, Structure of Chromium (III) Fluoride, *Short Communications*, 13, 507–508, 1960.

*Ullman's Encyclopedia of Industrial Chemistry*, Fifth Ed., vol. A7, 83 (1977).

L.E. Manzer et al., *Adv. Catal.*, 39, 329–350, 1993.

*Primary Examiner*—Johann Richter
*Assistant Examiner*—Jane C. Richter

[57] ABSTRACT

This invention provides a process for the manufacture of a fluoroolefin of the formula $(R^1)_2C=C(R^1)_2$ wherein each $R^1$ is independently selected from the group consisting of —H, —F, —CF$_3$, —CHF$_2$, —CH$_2$F, —C$_2$F$_5$, —C$_2$HF$_4$ and —C$_2$H$_2$F$_3$, provided that at least one $R^1$ is not —H. The process comprises contacting a hydrofluorocarbon of the formula $(R^1)_2$CHCF$(R^1)_2$ with a catalyst comprising cubic chromium trifluoride, i.e., a chromium trifluoride having an X-ray diffraction powder pattern shown in Table I, at a temperature of from about 200° C. to about 500° C.

5 Claims, No Drawings

FLUOROOLEFIN MANUFACTURING PROCESS

This application claims the priority benefit of U.S. Provisional Application 60/056,793, filed Aug. 25, 1997.

FIELD OF THE INVENTION

This invention relates to processes for the production of fluoroolefins, and more particularly, to a catalytic process using chromium-containing catalysts for the dehydrofluorination of hydrofluorocarbons to fluorooolefins.

BACKGROUND

Fluoroolefins are useful as monomers for fluoropolymers. For example, vinyl fluoride is a useful monomer for the preparation of fluorocarbon polymers which have excellent weathering and chemical resistance properties.

U.S. Pat. No. 2,599,631 discloses a process for the manufacture of vinyl fluoride by the dehydrofluorination of HFC-152a. The dehydrofluorination is done in the presence or absence of a catalyst. The dehydrofluorination catalysts disclosed include oxygen, charcoal, and the free metals, salts and oxides of the elements of Groups IA, IB, IIA, IIB, VB and VIII of the periodic table.

PCT Publication No. WO 96/05157 discloses a process for the dehydrofluorination of $CH_2FCF_3$ to $CHF=CF_2$ using Lewis acid catalysts. These catalysts include chromia ($Cr_2O_3$), chromia doped with metals such as nickel, cobalt, zinc, iron and copper. Other disclosed catalysts include aluminum fluoride and materials comprising a fluorine containing Lewis acid.

$CrF_3$ has been reported to form rhombohedral crystals (see e.g., Ullman's Encyclopedia of Industrial Chemistry, Fifth Ed., Vol. A7, p. 83). There is an ongoing interest in developing efficient catalysts for the conversion of hydrofluorocarbons to fluoroolefins.

SUMMARY OF THE INVENTION

This invention provides a process for the manufacture of a fluoroolefin of the formula $(R^1)_2C=C(R^1)_2$ wherein each $R^1$ is independently selected from the group consisting of —H, —F, —$CF_3$, —$CHF_2$, —$CH_2F$, —$C_2F_5$, —$C_2HF_4$ and —$C_2H_2F_3$, provided that at least one $R^1$ is not —H. The process comprises contacting a hydrofluorocarbon of the formula $(R^1)_2CHCF(R^1)_2$ with a catalyst comprising cubic chromium trifluoride (i.e., a chromium trifluoride having an X-ray diffraction powder pattern as shown in Table I) at a temperature of from about 200° C. to about 500° C.

DETAILED DISCUSSION

This invention involves cubic chromium trifluoride, a composition having an X-ray diffraction powder pattern as shown in Table I, as follows:

TABLE I

| Powder X-ray diffraction Data for Cubic-CrF$_3$ | | | | |
|---|---|---|---|---|
| d spacing (Å) | Relative intensity[a] | H | K | L |
| 5.8888 | VS[b] | 1 | 1 | 1 |
| 3.0674 | S[c] | 3 | 1 | 1 |
| 2.9423 | M[d] | 2 | 2 | 2 |
| 2.0818 | W[e] | 4 | 2 | 2 |
| 1.9547 | W[e] | 5 | 1 | 1 |
| 1.7991 | M[d] | 4 | 4 | 0 |

[a]as recorded at room temperature using a conventional diffractometer such as SCINTAG (PAD IV) diffractometer with copper k-alpha radiation
[b]VS means very strong (e.g., a relative intensity of about 100)
[c]S means strong (e.g., a relative intensity of about 46)
[d]M means moderate (e.g., a relative intensity of about 33 and about 14 for d spacing of 2.9423 and 1.7991, respectively)
[e]W means weak (e.g., a relative intensity of about 7 and about 4 for d spacing Cubic chromium trifluoride may be prepared from $CrF_3 \cdot XH_2O$, where X is 3 to 9, preferably 4, by heating in air or an inert atmosphere (e.g., nitrogen or argon) at 350° C. to 400° C. for 3 to 12 hours, preferably 3 to 6 hours. The color of cubic chromium trifluoride is dark green.

Cubic chromium trifluoride is useful by itself and together with other chromium compounds, as a catalytic material. Of note are catalyst compositions comprising chromium wherein at least 10% of the chromium is in the form of cubic chromium trifluoride, particularly catalyst compositions wherein at least 25% of the chromium is in the form of cubic chromium trifluoride, and especially catalyst compositions wherein at least 60% of the chromium is in the form of cubic chromium trifluoride. The chromium, including the cubic chromium trifluoride can be supported on and/or physically mixed with materials such as carbon, aluminum fluoride, fluorided alumina, lanthanum fluoride, magnesium fluoride, calcium fluoride, zinc fluoride and the like. Preferred are combinations including cubic chromium trifluoride in combination with magnesium fluoride and/or zinc fluoride. Chromium trifluoride catalyst which consists essentially of cubic chromium trifluoride can also be prepared and used in accordance with this invention.

The cubic chromium trifluoride-containing catalyst may be of various physical shapes, including for example, pellets, powders and granules.

This invention provides a process for producing fluoroolefins of the formula $(R^1)_2C=C(R^1)_2$ from corresponding hydrofluorocarbons of the formula $(R^1)_2CHCF(R^1)_2$. This process includes a method for producing 1-fluoroethene (i.e., $CH_2=CHF$ or 1141) from 1,1-difluoroethane (i.e., $CH_3CHF_2$ or HFC-152a); for producing 1,1,2-trifluoroethene (i.e., $CHF=CF_2$ or 1123) from 1,1,2,2-tetrafluoroethane (i.e., $CHF_2CHF_2$ or HFC-134) or 1,1,1,2-tetrafluoroethane (i.e., $CH_2FCF_3$ or HFC-134a). HFC-152a, HFC-134 and HFC-134a can all be prepared by known art methods.

This process also includes a method for producing cis- and trans-1,2,3,3,3-pentafluoropropene (i.e., $CF_3CF=CHF$ or 1225ye) from 1,1,1,2,3,3-hexafluoropropane (i.e., $CF_3CHFCHF_2$, or HFC-236ea). A process is also provided for producing 1,1,3,3,3-pentafluoropropene (i.e., $CF_3CH=CF_2$ or 1225zc) from 1,1,1,3,3,3-hexafluoropropane (i.e., $CF_3CH_2CF_3$, or HFC-236fa). Another process provided is a method for producing cis- and trans-1,2,3,3-tetrafluoropropene (i.e., $CHF_2CF=CHF$ or 1234ye) and 1,1,2,3-tetrafluoropropene (i.e., $CH_2FCF=CF_2$ or 1234yc) from 1,1,2,2,3-pentafluoropropane (i.e., $CH_2FCF_2CHF_2$, or HFC-245ca). Also provided is a process for producing cis- and trans-1,3,3,3-tetrafluoropropene (i.e., $CF_3CH=CHF$ or 1234ze) and 1,1,3,3-tetrafluoropropene (i.e., $CHF_2CH=CF_2$ or 1234zc) from 1,1,1,3,3- pentafluoropropane (i.e., $CHF_2CH_2CF_3$ or HFC-245fa). HFC-236ea, HFC-236fa, HFC-245ca and HFC-245fa can all be prepared by known art methods. For example, $CF_3CH_2CF_3$ can be prepared by contacting a mixture of hydrogen fluoride and 1,1,1,3,3,3-hexachloropropane (i.e., $CCl_3CH_2CCl_3$) in the vapor phase in the presence of a trivalent chromium catalyst as disclosed in U.S. Pat. No. 5,414,165 and $CF_3CHFCHF_2$ can be prepared by hydrogenation of hexafluoropropene (i.e., $CF_3CF=CF_2$) in the presence of a Pd/C catalyst.

The dehydrofluorination process further includes a method for producing 1,1,2,3,3,4,4-heptafluorobutene (i.e., $CF_2=CFCF_2CHF_2$ or 1327pc) from 1,1,2,2,3,3,4,4-octafluorobutane (i.e., $CHF_2CF_2CF_2CHF_2$ or HFC-338pcc), and cis- and trans-1,1,1,2,4,4,5,5,5-nonafluoropentene-2 (i.e., $CF_3CF=CHCF_2CF_3$ or 1429myz) cis- and trans-1,1,1,3,4,4,5,5,5-nonafluoropentene-2 (i.e., $CF_3CH=CFCF_2CF_3$ or 1429mzy) from 1,1,1,2,3,4,4,5,5,5-decafluoropentane (i.e., $CF_3CHFCHFCF_2CF_3$ or HFC-43-10mee). Both HFC-338pcc and HFC-43-10mee can be prepared by known art methods.

In a preferred embodiment, the catalytic dehydrofluorination of $CH_3CHF_2$ is suitably conducted at a reaction temperature within the range of from about 200° C. to about 400° C., preferably about 225° C. to 375° C. To provide for low acetylene formation and to enhance catalyst life, the temperature is preferably kept within the range of from about 250° C. to about 350° C., more preferably, from about 250° C. to about 325° C.

The 1,1-difluoroethane is typically passed over the catalyst at a rate of about 60 volumes to about 3600 volumes per volume of catalyst per hour; preferably 120 volumes to 720 volumes per volume of catalyst per hour. These volumes correspond to a contact time of about 60 seconds to about 1 second and preferably about 30 seconds to about 5 seconds. Normally a contact time is employed which is sufficient to provide a dehydrofluorination of HFC-152a equal to at least 50% of the equilibrium value for conversion of 1,1-difluoroethane to vinyl fluoride at the temperature employed; preferably at least 80%, and more preferably at least 90% of the equilibrium value at a given reaction temperature.

Unreacted starting material can be recycled to the reactor for the production of additional $CH_2=CHF$. Vinyl fluoride (b.p. −72° C.) may be recovered from the reaction product and any unreacted 1,1-difluoroethane (b.p. −25° C.) by conventional procedures such as distillation.

The catalytic dehydrofluorination of hydrofluorocarbons of the formula $(R^1)_2CHCF(R^1)_2$ is suitably conducted at a temperature in the range of from about 200° C. to about 500° C. and preferably from about 225° C. to about 400° C. The contact time is typically from about 1 to about 450 seconds, preferably from about 10 to about 120 seconds.

The reaction pressure can be subatmospheric, atmospheric or superatmospheric. Generally, near atmospheric pressures are preferred. However, the dehydrofluorination of $CF_3CH_2CF_3$ can be beneficially run under reduced pressure (i.e., pressures less than one atmosphere).

The reaction can also be done in the presence of inert gases which are stable under the reaction conditions such as nitrogen and argon.

Unreacted starting hydrofluorocarbons can be recycled to the reactor for the production of additional fluoroolefins. The fluoroolefines may be recovered from the reaction product and any unreacted hydrofluorocarbons by conventional procedures such as distillation.

The dehydrofluorination process of this invention can be carried out readily in the vapor phase using well known chemical engineering practice.

The reaction zone and its associated feed lines, effluent lines and associated units should be constructed of materials resistant to hydrogen fluoride. Typical materials of construction, well-known to the fluorination art, include stainless steels, in particuiar of the austenitic type, the well-known high nickel alloys, such as Monel® nickel-copper alloys, Hastelloy® nickel-based alloys and, Inconel® nickel-chromium alloys, and copper-clad steel. Silicon carbide is also suitable for reactor fabrication.

Without further elaboration, it is believed that one skilled in the art can, using the description herein, utilize the present invention to its fullest extent. The following specific embodiments are to be construed as illustrative, and not as constraining the remainder of the disclosure in any way whatsoever.

EXAMPLES

Example I

Preparation of Cubic Chromium Trifluoride

Commercial rhombohedral $CrF_3.4H_2O$ (about 3 g) was placed in a gold container and heated to 400° C. for 3–12 hours in air. The product was recovered and characterized. Powder x-ray diffraction measurements were recorded at room temperature using a SCINTAG (PAD IV) commercial diffractometer and indicated that the crystal structure of the product formed can be indexed as cubic with a lattice parameter of 10.201 Å (Table 2). The samples were weighed before and after the experiments. Weight loss measurements showed the compound formed at 400° C./6 hours is $CrF_3$ (Table 1) as shown in the equation,

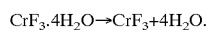

(Weight loss observed: 39.8%, Weight loss calculated 39.77%). The intensities of X-ray diffraction data show the compound has a face-centered cubic unit cell with space group Fd3m.

TABLE I-1

| Temp./time | Obs. weight loss | Phase formation |
|---|---|---|
| 200° C./12 hr | 25.6% | Amorphous |
| 250° C./6 hr | 28.4 | Amorphous |
| 300° C./6 hr | 31.1% | Amorphous + Cubic |
| 350° C./12 hr | 39.3% | Cubic |
| 400° C./3 hr | 38.6% | Cubic |
| 400° C./6 hr | 39.8% | Cubic |
| 400° C./12 hr | 51.0% | Amorphous + Cubic |
| 500° C./3 hr | 52.4% | $CrOF_2 + Cr_2O_3$ + amor. + Cubic |

TABLE I-2

Powder X-ray diffraction Data for Cubic-$CrF_3$
($CrF_3.4H_2O$, 400° C./6 hours)

| d spacing (Å) | Relative Intensity | H | K | L |
|---|---|---|---|---|
| 5.8888 | 100 | 1 | 1 | 1 |
| 3.0674 | 46 | 3 | 1 | 1 |
| 2.9423 | 33 | 2 | 2 | 2 |
| 2.0818 | 7 | 4 | 2 | 2 |
| 1.9547 | 4 | 5 | 1 | 1 |
| 1.7991 | 14 | 4 | 4 | 0 |

Catalyst Preparation for Use

Commercial $CrF_3.4H_2O$ (about 54 g) was placed in a gold container and heated to 400° C. for 3 hours. The product was granulated to form 1.2 to 1.7 mm particles for catalytic evaluation. The granulated product was subsequently treated with anhydrous HF at 400° C. for 4 hours as described below. The x-ray diffraction powder pattern of the product was essentially the same as that given for cubic $CrF_3$ in Table I-2.

General Procedure for HF Treatment of Cubic $CrF_3$

The granulated catalyst (9.2 g, 10 mL) was placed in a 5/8" (1.58 cm) Inconel® nickel alloy reactor heated in a fluidized sand bath. It was heated to 175° C. in a flow of nitrogen (50 cc/min) at which time HF flow (50 cc/min) was also started through the reactor. After 15 minutes, the nitrogen flow was decreased to 20 cc/min and the HF flow increased to 80 cc/min. The reactor temperature was gradually increased to 400° C. during a 2 hour period and maintained at 400° C. for an additional 30 minutes. At the end of this period the reactor was brought to the desired operating temperature for catalyst evaluation under a nitrogen flow of 10 cc/min and an HF flow of 50 cc/min.

General Procedure for Product Analysis

The following general procedure is illustrative of the method used. Part of the total reactor effluent was sampled on-line for organic product analysis using a Hewlett Packard HP 5890 gas chromatograph equipped with a 20' (6.1 m) long×1/8" (0.32 cm) diameter tubing containing Krytox® perfluorinated polyether on an inert carbon support. The helium flow was 35 mL/min. Gas chromatographic conditions were 70° C. for an initial hold period of three minutes followed by temperature programming to 180° C. at a rate of 6° C./minute. Unless indicated, the reported results are in mole %.

The bulk of the reactor effluent containing organic products and also inorganic acids such as HCl and HF was treated with aqueous caustic to neutralize the acids prior to disposal.

| Legend | |
| --- | --- |
| F1140 is $CH_2$=CHCl | F1141 is $CH_2$=CHF |
| F151a is $CH_3CHClF$ | F152a is $CH_3CHF_2$ |
| F143a is $CF_3CH_3$ | F236fa is $CF_3CH_2CF_3$ |
| F236ea is $CF_3CHFCHF_2$ | F1225ye is $CF_3CF$=CHF |
| F1225zc is $CF_3CH$=$CF_2$ | F43-10mee is $CF_3CHFCHFCF_2CF_3$ |
| F1429 is $C_5HF_9$ | |

Example 1

Dehydrofluorination of F152a $$CH_3CHF_2 \rightarrow CH_2=CHF$$

The General Procedures for HF Treatment of Cubic $CrF_3$ and Product Analysis were used. The organic feed composition to the reactor was 96.7% F152a, 2.7% F1141, 0.4% F1140 and 0.1% F151a. The F152a flow rate was 50 cc/min. and the contact time was 6 seconds. Results at various temperatures are shown in Table 1.

TABLE 1

| TEMP. ° C. | F1141 | F152a | Others[a] |
| --- | --- | --- | --- |
| 260 | 26.2 | 73.0 | 0.7 |
| 270 | 31.0 | 68.0 | 0.8 |
| 280 | 33.7 | 65.4 | 0.8 |

TABLE 1-continued

| TEMP. ° C. | F1141 | F152a | Others[a] |
| --- | --- | --- | --- |
| 290 | 35.1 | 63.9 | 0.9 |
| 320 | 47.3 | 51.5 | 0.9 |

[a]Others include F1140

Comparative Example A

Dehydrofluorination of F152a

The General Procedures for HF Treatment of Cubic $CrF_3$ and Product Analysis were used. However, the catalyst that was used was rhombohedral chromium trifluoride (9.5 g, 10 mL, 12 to 20 mesh (1.68 to 0.84 mm)). The organic feed composition to the reactor was 97.7% F152a, 2.0% F1141, 0.3% F1140 and 0.1% F151a. The F152a flow rate was 50 cc/min. and the contact time was 12 seconds. Results at various temperatures are shown in Table A.

TABLE A

| TEMP. ° C. | F1141 | F152a | Others[a] |
| --- | --- | --- | --- |
| 260 | 18.2 | 80.0 | 1.8 |
| 280 | 30.0 | 68.1 | 1.8 |
| 300 | 40.0 | 58.0 | 1.9 |

[a]Others include F1140

Example 2

Dehydrofluorination of F236fa $$CF_3CH_2CF_3 \rightarrow CF_3CH=CF_2$$

The General Procedures for HF Treatment of Cubic $CrF_3$ and Product Analysis were used, except that 4.64 g (5 mL) of catalyst was used. The organic feed composition to the reactor was 99.9% F236fa. The F236fa flow rate, contact time and results at various temperatures are shown in Table 2.

TABLE 2

| Temp. ° C. | Flow cc/min. | C.T. sec. | F143a | F1225zc | F236fa | Others |
| --- | --- | --- | --- | --- | --- | --- |
| 300 | 10 | 30 | 0 | 0.3 | 99.7 | — |
| 325 | 5 | 60 | 0.3 | 3.0 | 96.3 | 0.5 |
| 350 | 5 | 60 | 0.4 | 7.6 | 91.5 | 0.6 |
| 375 | 5 | 60 | 0.5 | 12.4 | 86.3 | 0.7 |
| 400 | 5 | 60 | 0.7 | 18.5 | 79.7 | 1.1 |

Example 3

Dehydrofluorination of F236ea $$CF_3CHFCHF_2 \rightarrow CF_3CF=CHF$$

The General Procedures for HF Treatment of Cubic $CrF_3$ and Product Analyis were used, except that 4.64 g (5 mL) of catalyst was used. The organic feed composition to the reactor was 99.9% F236ea. The F236ea flow rate was 5 cc/min. and the contact time was 60 seconds. Results at various temperatures are shown in Table 3.

TABLE 3

| Temp. (° C.) | F1225ye | F236ea | Others |
|---|---|---|---|
| 350 | 7.3 | 92.5 | 0.3 |
| 375 | 11.2 | 88.4 | 0.4 |
| 400 | 11.8 | 87.4 | 0.8 |

Example 4

Dehydrofluorination of F43-10mee
$CF_3CHFCHFCF_2CF_3 \rightarrow C_5HF_9$
$(CF_3CF=CHCF_2CF_3 + CF_3CH=CFCF_2CF_3)$ The General Procedures for HF Treatment of Cubic $CrF_3$ and Product Analysis were used, except that 4.64 g (5 mL) of catalyst was used. The organic feed composition to the reactor was 99.9% F4310mee. The F4310mee flow rate was 10 cc/min. and the contact time was 30 seconds. Results at various temperatures are shown in Table 4.

TABLE 4

| Temp. (° C.) | F1429 | F43-10mee | Others |
|---|---|---|---|
| 300 | 0.0 | 99.9 | 0.1 |
| 325 | 0.6 | 99.3 | 0.1 |
| 375 | 17.8 | 81.0 | 1.2 |
| 400 | 26.3 | 71.8 | 1.9 |

We claim:

1. A process for the manufacture of a fluoroolefin of the formula $(R^1)_2C=C(R^1)_2$ wherein each $R^1$ is independently selected from the group consisting of —H, —F, —$CF_3$, —$CHF_2$, —$CH_2F$, —$C_2F_5$, —$C_2HF_4$ and —$C_2H_2F_3$, provided that at least one $R^1$ is not —H, comprising:

contacting a hydrofluorocarbon of the formula $(R^1)_2CHCF(R^1)_2$ with a catalyst at temperature of from about 200° C. to about 500° C., said catalyst comprising cubic chromium trifluoride having the following X-ray diffraction powder pattern.

| d spacing (Å) | Relative intensty | H | K | L |
|---|---|---|---|---|
| 5.8888 | VS | 1 | 1 | 1 |
| 3.0674 | S | 3 | 1 | 1 |
| 2.9432 | M | 2 | 2 | 2 |
| 2.0818 | W | 4 | 2 | 2 |
| 1.9547 | W | 5 | 1 | 1 |
| 1.7991 | M7 | 4 | 4 | 0. |

2. The process of claim 1 wherein $CH_3CHF_2$ is dehydrofluorinated to $CH_2=CHF$.

3. The process of claim 1 wherein $CF_3CH_2CF_3$ is dehydrofluorinated to $CF_3CH=CF_2$.

4. The process of claim 1 wherein $CF_3CHFCHF_2$ is dehydrofluorinated to $CF_3CF=CHF$.

5. The process of claim 1 wherein $CF_3CHFCHFCF_2CF_3$ is dehydrofluorinated to $C_5HF_9$.

* * * * *